United States Patent [19]

Kraszewski et al.

[11] Patent Number: 5,039,947

[45] Date of Patent: Aug. 13, 1991

[54] MICROWAVE TECHNIQUE FOR SINGLE KERNEL, SEED, NUT, OR FRUIT MOISTURE CONTENT DETERMINATION

[75] Inventors: Andrzej W. Kraszewski; Stuart O. Nelson, both of Athens, Ga.

[73] Assignee: The United States of America as represented by the Secretary of Agriculture, Washington, D.C.

[21] Appl. No.: 532,294

[22] Filed: Jun. 1, 1990

[51] Int. Cl.$^5$ .................................................. G01N 22/04
[52] U.S. Cl. .................................... 324/634; 324/636
[58] Field of Search ............... 324/630, 633, 634, 636; 73/73

[56] References Cited

U.S. PATENT DOCUMENTS

| | | | |
|---|---|---|---|
| 4,211,970 | 7/1980 | Fitzky et al. | 324/634 |
| 4,257,001 | 3/1981 | Partain et al. | 324/636 |
| 4,297,874 | 11/1981 | Sasaki | 324/634 X |
| 4,781,063 | 11/1988 | Osaki et al. | 324/633 X |
| 4,801,862 | 1/1989 | Osaki et al. | 324/636 X |

OTHER PUBLICATIONS

A. W. Kraszewski et al., 1989 SBMO International Microwave Symposium Proceedings, vol. 1, pp. 85–90, Sao Paulo, Brazil, Jul. 24–27, 1989.
A. W. Kraszewski et al., 1989 IEEE MIT–S Digest, vol. 1, pp. 187–190, Jun. 13–15, 1989.
A. W. Kraszewski et al., IEEE Transactions on Instrumentation and Measurement, vol. 38, No. 1, pp. 79–84, Feb. 1989.
H. E. Bussey, Proceedings of the IEEE, vol. 55, No. 6, pp. 1046–1053, Jun. 1967.
Erratum, H. E. Bussey, Proceedings of the IEEE, vol. 56, No. 4, p. 729, Apr. 1968.

*Primary Examiner*—Jack B. Harvey
*Attorney, Agent, or Firm*—M. Howard Silverstein; John D. Fado; Randall E. Deck

[57] ABSTRACT

A process for nondestructively determining the moisture content of single articles such as single grain kernels, seeds, nuts, fruits, or other biological or agricultural products. The article is inserted into a microwave resonant cavity coupled to a microwave radiation source and a measuring circuit. Measurements of the energy dissipated in the sample and the shift in frequency (or wavelength) due to the presence of the article in the cavity are made at each of two orientations differing by about 90 degrees with respect to the maximum electric field vector. The moisture content is subsequently determined from the ratio of the averaged values of the energy dissipated to the shift in frequency. The process is particularly useful for determining the moisture content of articles of irregular or variable shape.

21 Claims, No Drawings

MICROWAVE TECHNIQUE FOR SINGLE KERNEL, SEED, NUT, OR FRUIT MOISTURE CONTENT DETERMINATION

BACKGROUND OF THE INVENTION

1. Field of Invention

This invention relates to the nondestructive measurement of the moisture content of individual single grain kernels, seeds, nuts, or fruits.

2. Description of the Prior Art

The moisture in cereal grains, seeds, nuts, and fruits is presently measured in bulk samples, and most of the available grain moisture meters are suitable for bulk samples only. The bulk values thus measured do not always represent the moisture content of every kernel in the bulk sample and do not provide any information on the range of moisture contents of the individual objects or kernels within the sample. Kandala ]M. S. Thesis, The University of Georgia, Athens, Ga. (1987)] reported earlier that single kernel moisture content in corn (maize), Zea mays L., can vary as much as ±0.8% on a wet basis (w.b.) from the bulk value as obtained by air-oven drying tests on single kernels and bulk samples from well-conditioned corn samples. Larger variations are expected in unconditioned samples. Further, the blending of grain with high levels of moisture with grain of permissible levels for safe storage can be conducive to the growth of microorganisms and may lead to spoilage. Concern has developed that spoilage of grain in transit or storage may be related to the practice of blending (mixing) of grain lots of different moisture levels.

Measurements of impedance on individual corn kernels with capacitive sensors at radio frequencies have been used to determine single kernel moisture content. Kandala et al. ]International Agrophysics 4(1-2): 3-12 (1988); Trans. ASAE 31(6): 1890-1895 (1988); Trans. ASAE 30(3): 793-797 (1987)] nondestructively measured the capacitance and dissipation factor of a small parallel plate capacitor with single kernels of corn between and in contact with the plates to determine kernel moisture content.

Electrical resistance of single kernels passing between crushing roller electrodes is also used for single kernel moisture determination.

Bussey ]Proc. IEEE 55(6): 1046-1053 (June 1967)] discussed the use of microwave resonant cavity techniques to measure the microwave and dielectric properties of materials by measuring the shift in the resonant frequency and the change in the Q-factor of the cavity when the sample is inserted into the cavity. However, Bussey did not disclose the measurement of the moisture contents of articles of variable or nonuniform shape.

Kraszewski et al. [IEEE Transactions on Instrumentation and Measurement 38(1): 79-84 (February 1989)] disclose a nondestructive process for the determination of moisture content in single soybean seeds using a microwave resonator. A seed is placed in a microwave resonant cavity and the resonant frequency shift and change in Q factor are measured. However, while this process allows the measurement of moisture content of articles of nearly uniform spherical shape, it does not provide for the accurate measurement of nonuniform, irregularly shaped objects.

SUMMARY OF THE INVENTION

We have now invented a method for nondestructively determining the moisture content of single articles such as single grain kernels, seeds, nuts, fruits, or other biological or agricultural products. According to the process, the sample article to be measured is inserted in a first position within a microwave resonant cavity coupled to a microwave radiation source and a measuring circuit. Subsequently, the energy dissipated in the sample article and the shift or change in the resonant frequency (or wavelength) due to the presence of the article in the cavity at the first position are measured. The orientation of the article in the cavity is then changed to a second position which is rotated by about $n \times 90$ degrees with respect to the maximum field vector (wherein n is an odd-numbered integer) and the measurements are repeated. Averaged values of the energy dissipated in the article and the shift in the resonant frequency (or wavelength) measured in the previous steps are calculated. The moisture content of the article is determined from the ratio of these averaged values. By conducting these measurements on articles of known moisture content, calibration equations or standard curves may be prepared which relate the moisture content of the article to the ratio of these averaged values.

The measurement of the energy dissipated in the sample article can be performed by measuring the change in the values of any one of the related parameters: the voltage transmission or reflection coefficient at resonance ($S_{21}$ or $S_{11}$), transmission factor (T), Q factor (Q), or the power transmission or reflection coefficient of the cavity. In essence, the complex values of the transmission and/or reflection coefficients must be measured as a function of frequency. This permits the shift of resonant frequency and the change in Q factor caused by the insertion of the article into the cavity to be determined.

In the alternative, rather than rotating the article by 90 degrees in the same cavity, two identical cavities could be provided and the article successively placed in each cavity but differing in orientation by approximately 90 degrees with respect to the maximum electric field vector. The first and second measurements would be conducted in the first and second cavities, respectively.

In accordance with this discovery, it is the primary objective of this invention to provide a method and apparatus for nondestructively measuring the moisture content of single grain kernels, seeds, nuts, fruits, or other biological or agricultural products with increased accuracy. The process is particularly useful in the determination of harvesting, processing, storage, and marketing operations for agricultural products or foods as well as research.

Another object of the invention is to provide a method using the measurement of the microwave dissipation of energy and shift in frequency caused by a single article to determine moisture content.

A further objective of the invention is to provide a method which is independent of the mass or shape or size of the article being measured. The method provides good predictability over a wide range of moisture contents for articles of variable or irregular shape.

DETAILED DESCRIPTION OF THE INVENTION

The process of the instant invention employs at least one microwave resonant cavity, means for coupling the cavity to a microwave radiation or energy source, and a measuring circuit allowing measurement of the transmission of microwave radiation through the cavity. A pair of identical cavities, each having respective coupling means and measuring circuits may also be provided. The measuring circuit performs at least two measurements: the shift or change in the resonant frequency (or wavelength) of the microwave radiation passing through the cavity, and the energy dissipated in the article within the cavity. As previously noted, the measurement of the energy dissipation includes any of measurement of the change in values of the parameters: voltage transmission coefficient at resonance ($S_{21}$), voltage reflection coefficient at resonance ($S_{11}$), transmission factor (T), Q-factor (Q), or the power transmission or reflection coefficient of the cavity. Means for suspending or otherwise removably fixing the position of the article in the cavity may also be provided. Means may also be provided for moving the article through the cavity or cavities. Such movement does not require any support or contact between the article and the cavity. A continuous flow of the articles of similar type may be provided so that the measurements are taken in a non-contacting way in each cavity, with one cavity rotated 90 degrees with respect to the other (when two cavities are used). Such means may include a line or guide receiving the articles or the articles may fall freely through the cavities or through a guiding tube therein.

The nondestructive process for determining the moisture content of a single article such as a single grain kernel, seed, nut, fruit, or other botanical or agricultural product according to the invention includes the steps of:

a) Inserting the single article into the microwave resonant cavity and orienting in a first position;

b) measuring both the energy dissipated in the article and the shift in resonant frequency (or wavelength) or the microwave radiation resulting from the presence of the article in the cavity relative to the empty cavity;

c) rotating or otherwise changing the orientation of the article by approximately 90 degrees or an odd-numbered multiple thereof with respect to the maximum electric field vector in the cavity to a second position;

d) repeating both of the measurements of step (b) with the article at the second position;

e) calculating both the average of the measured values of the energy dissipated and the average of the measured values of shift in resonant frequency (or wavelength) obtained in steps (b) and (d); and f) determining or calculating the moisture content of the article from the ratio of the average shift in frequency (or wavelength) to the average value of the energy dissipated in the article.

The final step of determining the moisture content may be conducted by comparison to standard curves of the ratio of these averaged parameters versus moisture content prepared from articles of the same type and known moisture content. Alternatively, the moisture content may be calculated by use of calibration equations derived by conventional techniques from measurements of articles of the same type having known moisture contents. For example, such calibration equations may be derived empirically by curve fitting techniques or algebraically as described in the following examples.

As mentioned above, between measurements using a single cavity, the article is rotated by approximately 90 degrees in any direction with respect to the maximum electric field vector. For instance, if the maximum E field vector is along the y-axis of the cavity, the article may be rotated 90 degrees about or around the x-axis or z-axis or about any line contained in the plane normal to the maximum E field vector. Further, it is understood that the step of "rotating" encompasses any step or steps wherein the orientation of the article is changed by approximately 90 degrees with respect to the maximum E field vector.

In an alternative embodiment, rather than rotating the article in the same cavity, two identical cavities could be provided and the measurements of steps (b) and (d) conducted in the first and second cavity, respectively. In this embodiment, the article is oriented in the second cavity in a second position which differs from the first position (in the first cavity) by approximately $n \times 90$ degrees with respect to the maximum E field vector in the cavities. Further, this difference in positions could be achieved by orienting the cavities to differ by 90 degrees to one another with contactless flow of articles through both of the cavities.

By measuring the two parameters for an article oriented in two positions differing by 90 degrees with respect to the maximum electric field vector, the ratio of the average values of the parameters has been found to be virtually shape independent. The ratio can be related to the article's moisture content, density, or other characteristic when all other properties remain unchanged.

The method can be used for virtually any single grain kernel, seed, nut, fruit, or other biological or agricultural product such as corn, soybeans, rice, wheat kernels, or kernels of any other grain provided that their volume is small compared to the volume of the resonator.

The microwave frequency and mode of operation of the cavity are not critical but will depend upon the resonant structure dimensions and the article for which the resonator is designed to measure moisture content. Microwave frequencies from 1 to 10 GHz are preferred, although frequencies below or above this range can be used. Similarly, the microwave resonant cavities may be rectangular, cylindrical, or spherical in shape or they may be any other suitable resonant structure.

EXAMPLE 1

A rectangular microwave cavity was provided which consisted of a section of standard WR-284 waveguide (inside dimensions, $72 \times 34$ mm) 305 mm long and was coupled with the external waveguides through two identical holes of 20.6 mm diam. The resonant frequency of the empty cavity operating in the $H_{105}$ mode was 3205.8 MHz and its Q-factor, $Q_{Lo}$, was 1650 (the empty cavity).

The cavity was located between two waveguide-to-coaxial transitions which allowed it to be connected to an automatic network analyzer calibrated in the transmission mode. We used 801 discrete frequency points with a range of 8 MHz spanning the resonant frequency of the cavity. This allowed measurement of the transmission through the cavity in increments of 10 kHz by reading coordinates of a marker position. A command "marker to maximum" accomplished the determination of the resonant frequency with accuracy better than 5 kHz and the transmission coefficient ($S_{21}$) through the cavity with an accuracy of 0.01 dB automatically.

EXAMPLE 2

Corn kernels used were from six hybrid, yellow-dent field corn cultivars grown in four different states in 1988 and stored at 4° C. after harvest. Corn kernels are highly nonuniform, irregularly shaped objects, sometimes pyramidal, cuboidal, or disk-like, up to 14 mm long, with no plane surfaces and seldom with surfaces parallel to each other. The maximum to minimum dimension ratio ranged from 1.3 to 4.0. Sixty-eight kernels were selected from six lots with initial moisture contents of about 18%, wet basis. Among these kernels, the highest to lowest weight ratio was 2.1. The kernels were permitted to dry under room conditions (23° C., 30% RH) for various time intervals and were then sealed in glass vials and held at 5° C. for at least 24 hr prior to measurement to obtain more uniform moisture distribution within the kernel. They were weighed after each microwave measurement to an accuracy of 0.2 mg. and finally were dried in a forced-air oven at 103° C. for 72 hr to determine the dry weight. Moisture content of each kernel at the time of microwave measurement was then calculated in order to complete the calibration. The same procedure was later applied to 36 kernels used in the verifying cavity measurements for moisture determination according to the process of the invention and as described in Kraszewski et al. [1989 SBMO Int. Microwave Symp. Proc., Vol. 1, pp. 85–90, Sao Paulo, Brazil (July 24–27, 1989)], the contents of which are herein incorporated by reference.

In this experimental laboratory approach, a 0.33-mm nylon line was passed through the individual kernels, permitting them to be held about the center of the cavity of Example 1 and rotated about the x-axis when the maximum electric field vector is along the y-axis. The measurement of the shift of the resonant frequency, f, is denoted as $\Delta F = f_o - f_s$, where the subscripts o and s refer to the empty cavity and the cavity loaded with a sample, respectively. The energy dissipated in the sample can be expressed in terms of changes in the cavity Q-factor as $$\frac{1}{Q_{Ls}} - \frac{1}{Q_{Lo}} = \frac{1}{Q_{Lo}}\left[\frac{Q_{Lo}}{Q_{Ls}} - 1\right] = \frac{\Delta T}{Q_{Lo}}.$$

Because the ratio of $Q_{Lo}/Q_{Ls} = V_o/V_s$, where V is the voltage transmission coefficient at resonance, which can be easily and accurately measured, the following transmission factor was used to describe the changes in cavity transmission characteristics:

$$\Delta T = 10^k - 1 \text{ where } k = 0.05\,(S_{21o} - S_{21s})$$

with $S_{21}$ being the measured value of the voltage transmission coefficient at resonance expressed in decibels. The shift of the resonant frequency $\Delta F$ and change in transmission factor $\Delta T$ were measured for each kernel at a first position, and subsequently at a second position with the kernels rotated 90 degrees about the x-axis, and the average values $\Delta T_{avg}$ and $\Delta F_{avg}$ calculated for each kernel.

To prepare the calibration equation, experimental results were accumulated for the 68 kernels measured at various hydration levels. The average shift in the resonant frequency, $\Delta F_{avg}$, as a function of the mass of water in the kernels was plotted in a first graph while the average change in transmission factor, $\Delta T_{avg}$, as a function of the mass of water was plotted in a second. Two linear expressions were derived, one from each graph, which fit the experimental results with a high statistical significance:

$$\Delta F_{avg} = 0.0783 + 0.06183\,M_w + 0.00669\,M_d \quad r = 0.9854 \quad (1)$$

$$\Delta T_{avg} = -0.00672 + 0.01637\,M_w - 0.00019\,M_d \quad r = 0.9646 \quad (2)$$

where $M_w$ and $M_d$ refer to the mass of water in the kernel and the dry mass of the kernel, respectively, and r is the correlation coefficient. Since the relative moisture content, MC, in percent, wet basis, is defined as $$MC = \frac{M_w}{M_w + M_d} \times 100 \quad (3)$$

algebraic solution of equations (1) and (2) for $M_w$ and $M_d$ and substitution into equation (3) provides a correlation equation for moisture content in corn kernels:

$$MC = \frac{X + 1.6\,(22.25 + Y)}{0.88\,(X - 3.33 - Y)} \quad (4)$$

where $X = \Delta F_{avg}/\Delta T_{avg}$ and $Y = 0.101/\Delta T_{avg}$.

To test the validity of the calibration equation (4), another 36 corn kernels with the highest-to-lowest dry weight ratio of more than 2 were randomly selected from the same lots, and 59 cavity measurements were taken over the moisture content range from 8 to 15% in the same manner described above. The exact moisture contents were determined by the standard oven method and compared with those calculated by the process of the invention using equation (4). The mean value of the difference was 0.08% moisture and the standard deviation of the difference was 0.81% moisture. Therefore, the calibration equation (4) can be used to determine the moisture content of corn kernels from this lot with an uncertainty of 1.6% moisture at the 95% confidence level.

EXAMPLE 3

A rectangular microwave cavity was provided in a manner similar to that described in Example 1 but operating in the $H_{107}$ mode at 6 GHz. Measurements of $\Delta F_{avg}$, $\Delta T_{avg}$, and moisture content (by oven drying) for 53 yellow dent field corn kernels of various hydration levels were obtained in the same manner of Example 2.

To prepare the calibration equation, the ratio, $\Delta F_{avg}/\Delta T_{avg}$, as a function of moisture content for corn kernels was plotted in a standard curve as described in Kraszewski et al. [1989 IEEE MIT-S Digest, Vol. 1, pp. 187–190 (June 13–15, 1989)], the contents of which are herein incorporated by reference. The calibration equation which was then derived by conventional curve fitting techniques expressed the moisture content as:

$$MC = \frac{281}{X} + 2.9 \quad (5)$$

where $X = \Delta F_{avg}/\Delta T_{avg}$ and the correlation coefficient $r = 0.94$.

To test the validity of the calibration equation (5), another 55 corn kernels were measured in the same manner described above. The exact moisture contents were determined by the standard oven method and compared with those calculated by the process of the invention using equation (5). The mean value of the differences was 0.02% moisture and the standard deviation of the difference was 0.62% moisture.

In the alternative to using calibration equation (5), it is recognized that the moisture content of the unknown corn kernels could be determined by comparison of the measured ratio $\Delta F_{avg}/\Delta T_{avg}$ to the standard curve of Example 3.

It is understood that the foregoing examples and detailed description are given merely by way of illustration and that variations may be made therein without departing from the spirit and scope of the invention.

We claim:

1. A nondestructive process for determining the moisture content of single grain kernels, seeds, nuts, fruits, or other botanical or agricultural products comprising the steps of:
   a. inserting a single article selected from the group consisting of grain kernels, seeds, nuts, fruits, and other botanical or agricultural products, oriented in a first position in a microwave resonant cavity, said cavity being coupled to a microwave radiation source and a measuring circuit allowing measurement of the transmission of microwave radiation through the cavity;
   b. measuring both of the energy dissipated in said article and the shift in the resonant frequency or wavelength of the microwave radiation resulting from the presence of said article in said cavity at said first position relative to an empty cavity;
   c. changing the orientation of said article in said cavity to a second position which differs by approximately $n \times 90$ degrees with respect to the maximum electric field vector in said cavity, and wherein n is an odd integer;
   d. measuring both of the energy dissipated in said article and the shift or change in the resonant frequency or wavelength of the microwave radiation resulting from the presence of said article in said cavity at said second position relative to an empty cavity;
   e. calculating the average of the energy dissipated and the average of the shift or change in the frequency or wavelength measured in steps (b) and (d);
   f. determining the moisture content of said article from the ratio of said average of the shift or change in the frequency or wavelength to said average of the energy dissipated.

2. The process of claim 1 wherein said steps of measuring the energy dissipated in said article comprise measuring the change in values of the parameters selected from the group consisting of the voltage transmission coefficient at resonance, voltage reflection coefficient at resonance, Q-factor, transmission factor, and the power transmission or reflection coefficient of said cavity.

3. The process of claim 2 wherein the said steps of measuring include measuring both the change in the voltage transmission or reflection coefficient at resonance and the shift in frequency of the microwave radiation, and calculating the change in the transmission factor from said change in voltage transmission or reflection coefficient.

4. The process of claim 1 wherein said article is selected from the group consisting of corn kernels, soybeans, rice, wheat kernels, and kernels of other grains.

5. The process of claim 1 wherein the frequency of the microwave radiation is about 1 to about 10 GHz.

6. The process of claim 1 wherein the frequency of the microwave radiation is less than 1 GHz.

7. The process of claim 1 wherein the frequency of the microwave radiation is greater than 10 GHz.

8. The process of claim 1 wherein said second position differs from said first position by 90 degrees with respect to the maximum electric field vector in said cavity.

9. The process of claim 1 wherein said step of changing the orientation comprises rotating said article in said cavity.

10. The process of claim 1 wherein said cavity is rectangular, cylindrical, or spherical in shape.

11. The process of claim 1 wherein said cavity contains means for continuous movement of said article through said cavity without contact between the article and said cavity, and said means for continuous movement orienting said article in said first and second positions.

12. A nondestructive process for determining the moisture content of single grain kernels, seeds, nuts, fruits, or other botanical or agricultural products comprising the steps of:
   a. inserting a single article selected from the group consisting of grain kernels, seeds, nuts, fruits, and other botanical or agricultural products, oriented in a first position in a first microwave resonant cavity, said cavity being coupled to a microwave radiation source and a measuring circuit allowing measurement of the transmission of microwave radiation through the cavity;
   b. measuring both of the enemy dissipated in said article and the shift in the resonant frequency or wavelength of the microwave radiation resulting from the presence of said article in said first cavity at said first position relative to an empty cavity;
   c. removing said article from said first cavity and inserting it into a second microwave resonant cavity identical to said first microwave resonant cavity, said second cavity being coupled to a microwave radiation source and a measuring circuit allowing measurement of the transmission of microwave radiation through the second cavity, said article being oriented in said second cavity in a second position which differs from said first position by approximately $n \times 90$ degrees with respect to the maximum electric field vector in said cavities, and wherein n is an odd integer;
   d. measuring both of the energy dissipated is said article and the shift or change in the resonant frequency or wavelength of the microwave radiation resulting from the presence of said article in said second cavity at said second position relative to an empty cavity;
   e. calculating the average of the energy dissipated and the average of the shift or change in the frequency or wavelength measured in steps (b) and (d);
   f. determining the moisture content of said article from the ratio of said average of the shift or change in the frequency or wavelength to said average of the energy dissipated.

13. The process of claim 12 wherein said steps of measuring the energy dissipated in said article comprise measuring the change in values of the parameters selected from the group consisting of the voltage transmission coefficient at resonance, voltage reflection coefficient at resonance, Q-factor, transmission factor, and the power transmission or reflection coefficient of said cavities.

14. The process of claim 13 wherein the said steps of measuring include measuring both the change in the voltage transmission or reflection coefficient at resonance and the shift in frequency of the microwave radiation in each cavity and calculating the change in the transmission factor from said change in the voltage transmission or reflection coefficient.

15. The process of claim 12 wherein said article is selected from the group consisting of corn kernels, soybeans, rice, wheat kernels, and kernels of other grains.

16. The process of claim 12 wherein the frequency of the microwave radiation in each cavity is about 1 to about 10 GHz.

17. The process of claim 12 wherein the frequency of the microwave radiation in each cavity is less than 1 GHz.

18. The process of claim 12 wherein the frequency of the microwave radiation in each cavity is greater than 10 GHz.

19. The process of claim 12 wherein said second position differs from said first position by 90 degrees with respect to the maximum electric field vector in said cavities.

20. The process of claim 12 wherein said cavities are rectangular, cylindrical, or spherical in shape.

21. The process of claim 12 wherein said first cavity is rotated by approximately 90 degrees with respect to said second cavity, said cavities containing means for continuous movement of said article through both of said cavities without contact between the article and said cavities, and said means for continuous movement orienting said article in said first and second positions.

* * * * *